United States Patent
Rockrohr

(10) Patent No.: US 10,779,897 B2
(45) Date of Patent: *Sep. 22, 2020

(54) ROBOTIC SURGICAL ASSEMBLIES

(71) Applicant: Covidien LP, Mansfield, MA (US)

(72) Inventor: Brian Rockrohr, Guilford, CT (US)

(73) Assignee: COVIDIEN LP, Mansfield, MA (US)

( * ) Notice: Subject to any disclaimer, the term of this patent is extended or adjusted under 35 U.S.C. 154(b) by 353 days.

This patent is subject to a terminal disclaimer.

(21) Appl. No.: 15/735,058

(22) PCT Filed: Jun. 20, 2016

(86) PCT No.: PCT/US2016/038367
§ 371 (c)(1),
(2) Date: Dec. 8, 2017

(87) PCT Pub. No.: WO2016/209769
PCT Pub. Date: Dec. 29, 2016

(65) Prior Publication Data
US 2019/0099227 A1    Apr. 4, 2019

Related U.S. Application Data

(60) Provisional application No. 62/183,363, filed on Jun. 23, 2015.

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02); *A61B 2034/302* (2016.02); *A61B 2034/305* (2016.02)

(58) Field of Classification Search
CPC ... A61B 17/068; A61B 17/28; A61B 17/2804; A61B 17/29; A61B 17/00234;
(Continued)

(56) References Cited

U.S. PATENT DOCUMENTS

| 7,793,812 B2 * | 9/2010 | Moore | ............ A61B 17/07207 227/176.1 |
| 10,420,620 B2 * | 9/2019 | Rockrohr | ............ F16H 25/2015 |

(Continued)

FOREIGN PATENT DOCUMENTS

| KR | 20110109475 A | 10/2011 |
| WO | 2011016640 A2 | 2/2011 |

(Continued)

OTHER PUBLICATIONS

ISR Written Opinion of PCT/US2016/038367 dated Sep. 12, 2016.
(Continued)

*Primary Examiner* — Dianne Dornbusch

(57) ABSTRACT

A surgical instrument for use with and for selective connection to an instrument drive unit includes an end effector, an instrument drive connector including a plurality of drive assemblies, and a plurality of drive members in mechanical cooperation with the instrument drive connector and the end effector. Each drive assembly of the plurality of drive assemblies includes a drive screw including an elongated threaded body and a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

20 Claims, 13 Drawing Sheets

(58) Field of Classification Search
CPC ... A61B 34/30; A61B 34/71; A61B 34/32002; A61B 2034/302; A61B 2034/303; A61B 2034/305
See application file for complete search history.

(56) References Cited

U.S. PATENT DOCUMENTS

| | | | |
|---|---|---|---|
| 2010/0331820 A1 | 12/2010 | Prisco et al. | |
| 2011/0174099 A1* | 7/2011 | Ross | A61B 17/00 74/89.32 |
| 2012/0116416 A1 | 5/2012 | Neff et al. | |
| 2012/0158013 A1* | 6/2012 | Stefanchik | B25J 9/1689 606/130 |
| 2013/0041403 A1* | 2/2013 | Cunningham | A61B 18/1445 606/208 |
| 2013/0282052 A1* | 10/2013 | Aranyi | A61B 17/07207 606/208 |
| 2013/0319706 A1* | 12/2013 | Nicholas | B25F 3/00 173/29 |
| 2014/0005653 A1* | 1/2014 | Shelton, IV | A61B 18/1442 606/33 |
| 2014/0252067 A1* | 9/2014 | Moore | A61B 17/072 227/177.1 |
| 2015/0080907 A1 | 3/2015 | Herrell et al. | |
| 2016/0303743 A1 | 10/2016 | Rockrohr | |

FOREIGN PATENT DOCUMENTS

| | | |
|---|---|---|
| WO | 2012-112888 A2 | 8/2012 |
| WO | 2015-088647 A1 | 6/2015 |

OTHER PUBLICATIONS

Extended European Search Report corresponding to counterpart Patent Appln. No. EP 16815110.8 dated Jan. 23, 2019.
Japanese Office Action dated Mar. 23, 2020 corresponding to counterpart Patent Application JP 2017-565916.
Chinese First Office Action dated Mar. 18, 2020 corresponding to counterpart Patent Application CN 201680036211.8.
Australian Examination Report No. 1 dated Feb. 13, 2020 corresponding to counterpart Patent Application AU 2016284040.

* cited by examiner

ROBOTIC SURGICAL ASSEMBLIES

CROSS-REFERENCE TO RELATED APPLICATIONS

This application claims the benefit of and priority to U.S. Provisional Patent Application No. 62/183,363, filed Jun. 23, 2015, the entire disclosure of which is incorporated by reference herein.

BACKGROUND

Robotic surgical systems have been used in minimally invasive medical procedures. Some robotic surgical systems included a console supporting a robot arm, and surgical instruments with different end effectors, such as forceps or a grasping tool, that were mounted to the robot arm via a wrist assembly. During a medical procedure, the end effector and the wrist assembly of the surgical instrument were inserted into a small incision (via a cannula) or a natural orifice of a patient to position the end effector at a work site within the body of the patient.

These surgical instruments had cables extending longitudinally from spools at a proximal end through an elongated shaft and the wrist assembly to the end effector. The cables were actuated by means of motors coupled to the spools when the surgical instrument was attached to the robot arm. The surgeon manipulated an input device of the robotic system and the robotic system actuated the motors to move the surgical instrument and end effector in a correlated manner.

The cables in the surgical instruments were prone to stretch during use. The stretching could cause end effector movement to lag that of the input device based on the amount of stretch. As a result, the surgical instrument and end effector may appear to move in a less correlated manner, which would limit the responsive performance of the robotic system.

There is a need to reduce cable stretch in robotic surgical instruments.

SUMMARY

In one aspect of the present disclosure, a surgical instrument for use with and for selective connection to an instrument drive unit includes an end effector defining a longitudinal axis, an instrument drive connector including a housing assembly and a plurality of drive assemblies at least partially disposed within the housing assembly, and a plurality of drive members in mechanical cooperation with the instrument drive connector and the end effector. Each drive assembly of the plurality of drive assemblies includes a drive screw including an elongated threaded body. The drive screw is rotatably supported within the housing assembly. The drive assembly also includes a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

Each drive screw of the plurality of drive assemblies may include a proximal end having an input drive coupler configured to receive rotational forces.

Each drive nut of the plurality of drive assemblies may include a first rail extending longitudinally along an outer surface thereof. The first rail may be slidingly disposed within a longitudinally extending channel formed within the housing assembly.

In some embodiments, the instrument drive connector includes a drive connector frame disposed within the housing assembly and in mechanical cooperation with the plurality of drive assemblies.

The drive connector frame may include a proximal end including a plurality of proximal bearings. Each bearing of the plurality of proximal bearings may be dimensioned to retain a proximal end of the drive screw of one of the plurality of drive assemblies.

The drive connector frame may include an elongated central shaft, and the plurality of proximal bearings may be disposed radially around the elongated central shaft.

The elongated central shaft may include a plurality of longitudinally extending grooves defined in an outer surface thereof. Each groove of the plurality of longitudinally extending grooves may be configured to slidingly receive a portion of a respective one of the plurality of drive members.

Each of the drive nuts of the plurality of drive assemblies may include a second rail extending longitudinally along an outer surface thereof. The second rail may be slidingly disposed within one of the plurality of longitudinally extending grooves of the elongated central shaft of the drive connector frame.

In some embodiments, each drive member includes a flexible distal end and a rigid proximal end. The proximal end may be secured to one of the drive nuts of the plurality of drive assemblies.

The plurality of drive members may include a first drive member and a second drive member, and the end effector may include first and second jaw members and first and second jaw pulleys. The first drive member may be engaged with the first jaw pulley and the second jaw member may be engaged with the second jaw pulley such that longitudinal translation of the first and/or second drive members yaws the first and second jaw members about a first pivot axis that is orthogonal to the longitudinal axis of the end effector and/or moves the first and/or second jaw members relative to each other.

The end effector may include a clevis pivotally mounted to a set of idler pulleys. The first and second jaw pulleys may be coupled to the clevis and the first and second drive members may be engaged with the set of idler pulleys such that longitudinal translation of the first and/or second drive members pitches the first and second jaw members about a second pivot axis that is orthogonal to both the first pivot axis and the longitudinal axis of the end effector.

In another aspect of the present disclosure, an instrument drive connector for selectively interconnecting a surgical instrument having an end effector that is configured to perform a function and an instrument drive unit that is configured to actuate the end effector, includes a housing assembly defining a bore, a plurality of drive assemblies at least partially disposed within the bore of the housing assembly, and a plurality of drive members in mechanical cooperation with the instrument drive connector and the end effector. Each drive assembly of the plurality of drive assemblies includes a drive screw including an elongated threaded body and is rotatably supported within the housing assembly, and a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

Each drive screw of the plurality of drive assemblies may include a proximal end having an input drive coupler configured to engage the instrument drive unit and to receive rotational forces.

Each drive nut of the plurality of drive assemblies may include a first rail extending longitudinally along an outer surface thereof. The first rail may be slidingly disposed within a longitudinally extending channel formed in the bore of the housing assembly.

In some embodiments, the instrument drive connector includes a drive connector frame disposed within the bore of the housing assembly and in mechanical cooperation with the plurality of drive assemblies.

The drive connector frame may include a proximal end including a plurality of proximal bearings. Each bearing of the plurality of proximal bearings may be dimensioned to retain a proximal end of the drive screw of one of the plurality of drive assemblies.

The drive connector frame may include an elongated central shaft, and the plurality of proximal bearings may be disposed radially around the elongated central shaft.

The elongated central shaft may include a plurality of longitudinally extending grooves defined in an outer surface thereof. Each groove of the plurality of longitudinally extending grooves may be configured to slidingly engage a portion of a respective one of the plurality of drive members.

Each of the drive nuts of the plurality of drive assemblies may include a second rail extending longitudinally along an outer surface thereof. The second rail may be slidingly disposed within one of the plurality of longitudinally extending grooves of the elongated central shaft of the drive connector frame.

In some embodiments, each drive member includes a flexible distal end and a rigid proximal end. The proximal end may be secured to one of the drive nuts of the plurality of drive assemblies.

Other aspects, features, and advantages will be apparent from the description, drawings, and the claims.

BRIEF DESCRIPTION OF THE DRAWINGS

The accompanying drawings, which are incorporated in and constitute a part of this specification, and in which corresponding reference characters indicate corresponding parts in each of the several views, illustrate embodiments of the disclosure and, together with a general description of the disclosure given above, and the detailed description of the embodiment(s) given below, serve to explain the principles of the disclosure, wherein.

DETAILED DESCRIPTION

In this disclosure, the term "distal" refers to a portion of a structure that is farther from a clinician, while the term "proximal" refers to a portion of the same structure that is closer to the clinician. As used herein, the term "subject" refers to a human patient or other animal. The term "clinician" refers to a doctor (e.g., a surgeon), nurse, or other care provider, and may include support personnel.

Figure 1:
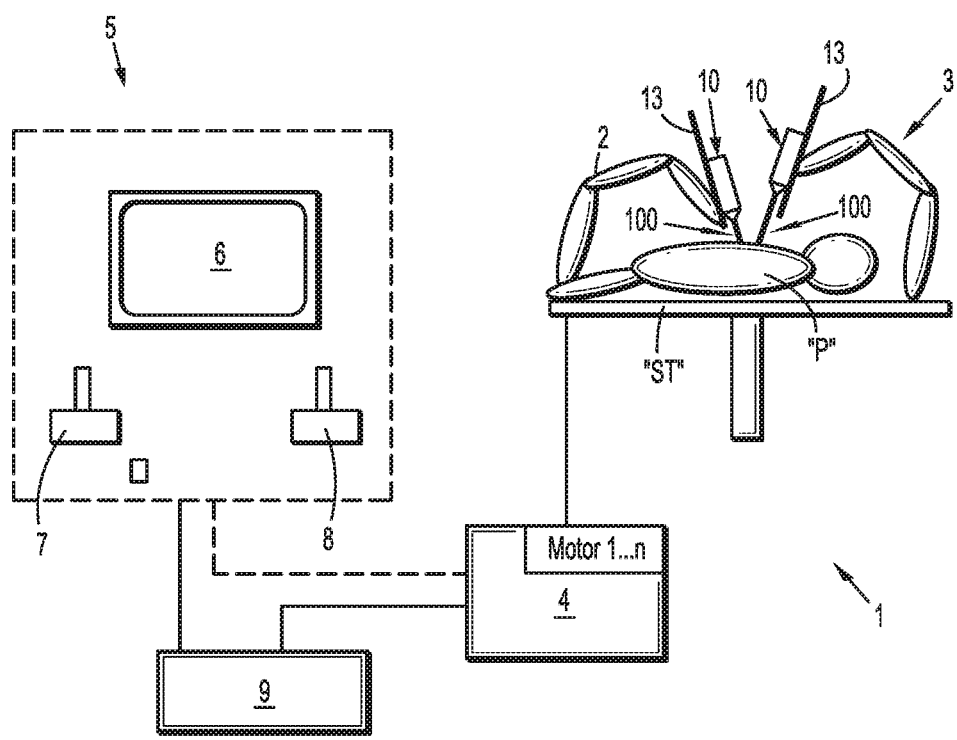
FIG. 1 is a schematic illustration of a robotic surgical system including a surgical assembly in accordance with the present disclosure.

Referring initially to FIG. 1, a robotic surgical system, such as, for example, medical work station 1, generally includes a plurality of robot arms 2 and 3, a control device 4, and an operating console 5 coupled with control device 4. Operating console 5 includes a display device 6, which is set up in particular to display three-dimensional images, and manual input devices 7 and 8, by means of which a clinician (not shown), for example a surgeon, is able to telemanipulate robot arms 2 and 3 in a first operating mode, as known in principle to a person skilled in the art.

Each of the robot arms 2 and 3 includes a plurality of members, which are connected through joints, to which may be attached, for example, a surgical assembly 10. Robot arms 2 and 3 may be driven by electric drives (not shown) that are connected to control device 4. Control device 4 (e.g., a computer) is set up to activate the drives, in particular by means of a computer program, in such a way that robot arms 2 and 3, the attached surgical assembly 10, and thus the surgical instrument 100 (including the end effector, not shown) execute a desired movement according to a movement defined by means of manual input devices 7 and 8. Control device 4 may also be set up in such a way that it regulates the movement of robot arms 2 and 3 and/or of the drives (not shown). Control device 4 may control a plurality of motors, e.g., "Motor 1 . . . n," with each motor configured to drive movement of robotic arms 2 and 3 in a plurality of directions.

Medical work station 1 is configured for use on a patient "P" lying on a surgical table "ST" to be treated in a minimally invasive manner by means of a surgical instrument 100 of surgical assembly 10. Medical work station 1 may also include more than two robot arms 2 and 3, the additional robot arms likewise being connected to control device 4 and being telemanipulatable by means of operating console 5. A surgical assembly 10 may also be attached to the additional robot arm. Medical work station 1 may include a database 9, in particular coupled to with control device 4, in which are stored for example pre-operative data from patient "P" and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Figure 2:
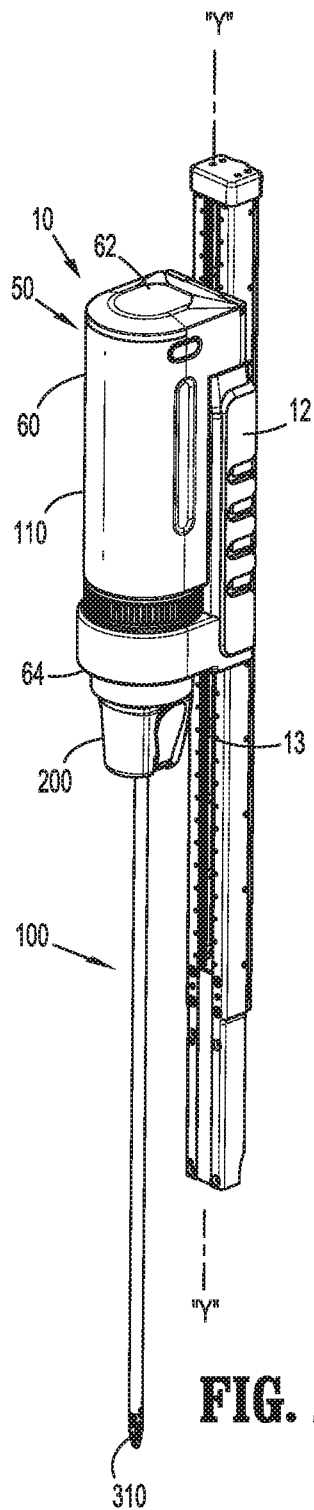
FIG. 2 is a perspective view of a surgical assembly of the robotic surgical system of FIG. 1.

Turning now to FIG. 2, in conjunction with FIG. 1, surgical assembly 10 is shown coupled with or to robotic arm 2. While surgical assembly 10 is discussed singularly, a person of ordinary skill in the art can readily appreciate that the medical work station 1 may also include a plurality of substantially identical surgical assemblies 10 coupled with or to each of the robotic arms 2 and 3. Surgical assembly 10 includes an instrument drive unit 50 coupled to an instrument drive connector 200 of a surgical instrument 100 having an end effector 310 disposed at a distal end thereof.

Instrument drive unit 50 of surgical assembly 10 may be supported on or connected to a slider 12 that is movably connected to a track or slide 13 of robotic arm 2. Slider 12 moves, slides, or translates along a longitudinal axis "Y" defined by track 13 of surgical robotic arm 2 upon a selective actuation by motors (not shown) disposed in track 13 of robotic arm 2 or motors (e.g., one or more of "Motor 1 . . . n") of control device 4. As such, slider 12, with instrument drive unit 50 connected thereto, can be moved to a selected position along track 13 of robotic arm 2.

Figure 3:
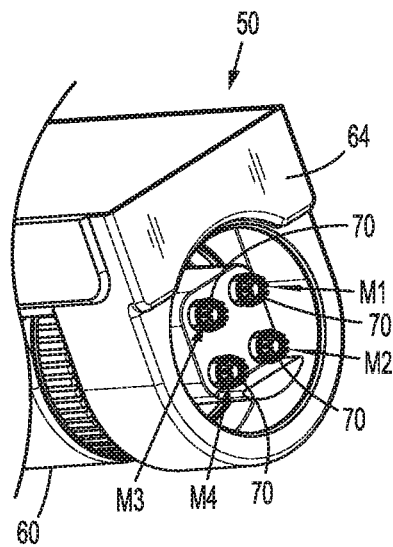
FIG. 3 is a perspective, end view of an instrument drive unit of the surgical assembly of FIG. 2.
Figure 4:
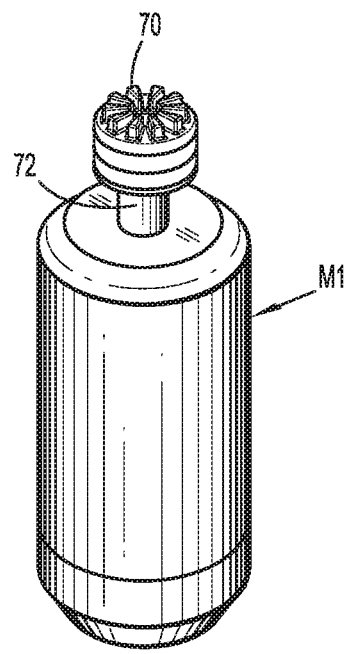
FIG. 4 is a schematic, perspective view of a motor of the instrument drive unit of FIG. 3.

With reference now to FIGS. 2 and 3, instrument drive unit 50 of surgical assembly 10 includes a housing 60 having a proximal end 62 and a distal end 64 configured to be operably coupled to instrument drive connector 200 of surgical instrument 100. Housing 60 of instrument drive unit 50 houses a plurality of motors "M1-M4" that are configured to drive various operations of end effector 310 of surgical instrument 100. Each motor "M1-M4" of instrument drive unit 50, as shown in an exemplary illustration of motor "M1" in FIG. 4, includes an output drive coupler 70 supported on a rotatable shaft 72 extending distally from the motor. In some embodiments, output drive couplers 70 are crown gears or the like, that are keyed to or non-rotatably supported on rotatable shafts 72 of at least one of motors "M1-M4." In use, instrument drive unit 50 transfers power and actuation forces from its motors (e.g., "M1-M4") to instrument drive connector 200 of surgical instrument 100 via rotation of output drive coupler(s) 70 to ultimately drive movement of components of end effector 310 of surgical instrument 100, as described in further detail below.

Control device 4 (FIG. 1) may control motors "M1-M4" of instrument drive unit 50. In some embodiments, at least one motor "M1-M4" receives signals wirelessly (e.g., from control device 4). It is contemplated that control device 4 coordinates the activation of the various motors ("Motor 1 . . . n") to coordinate an operation and/or movement of surgical instrument 100. It is envisioned that one or more motors correspond to a separate degree of freedom of surgical instrument 100 engaged with instrument drive unit 50.

Figure 5:
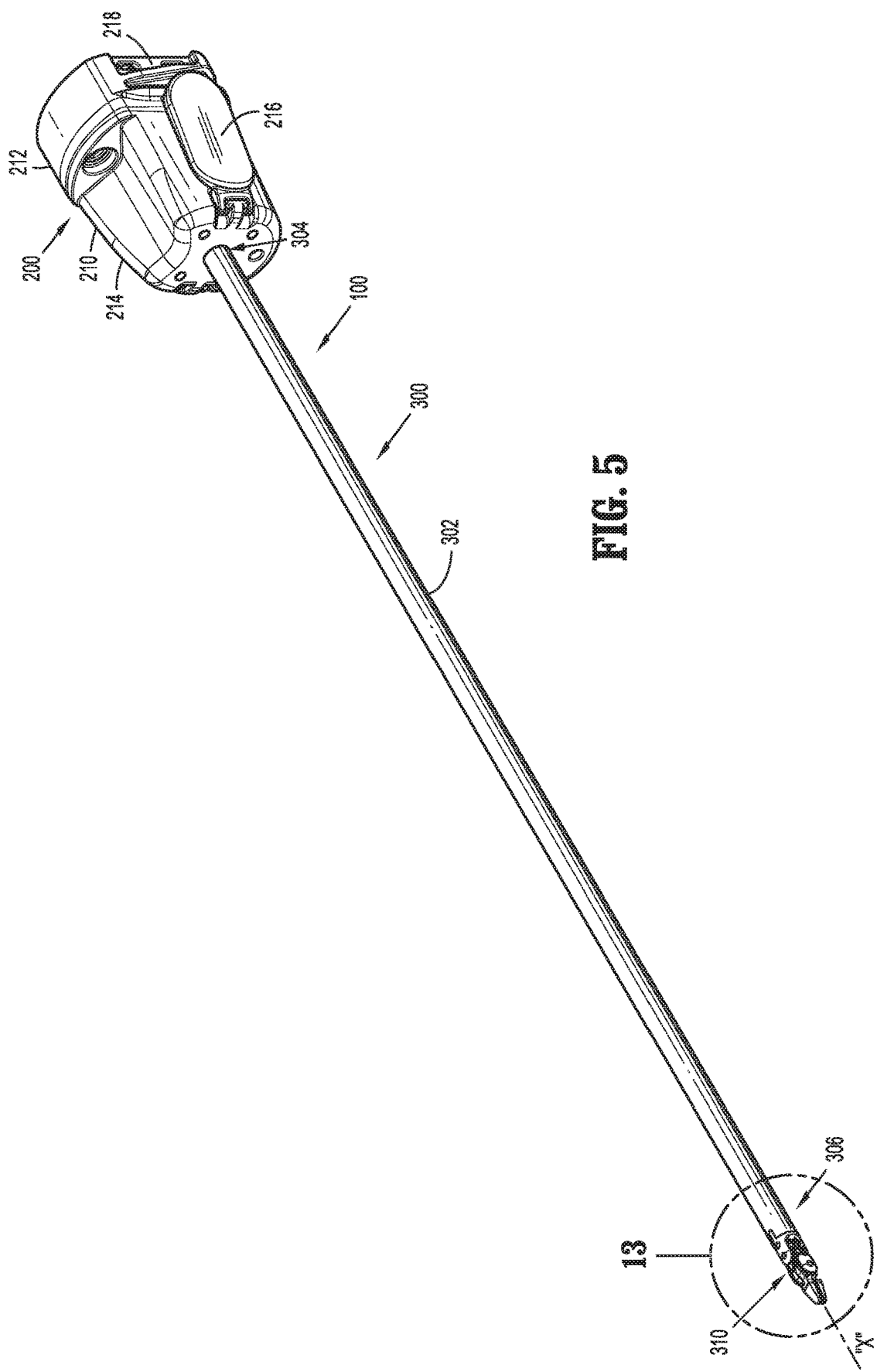
FIG. 5 is a perspective view of a surgical instrument of the surgical assembly of FIG. 2 including an instrument drive connector.
Figure 6:
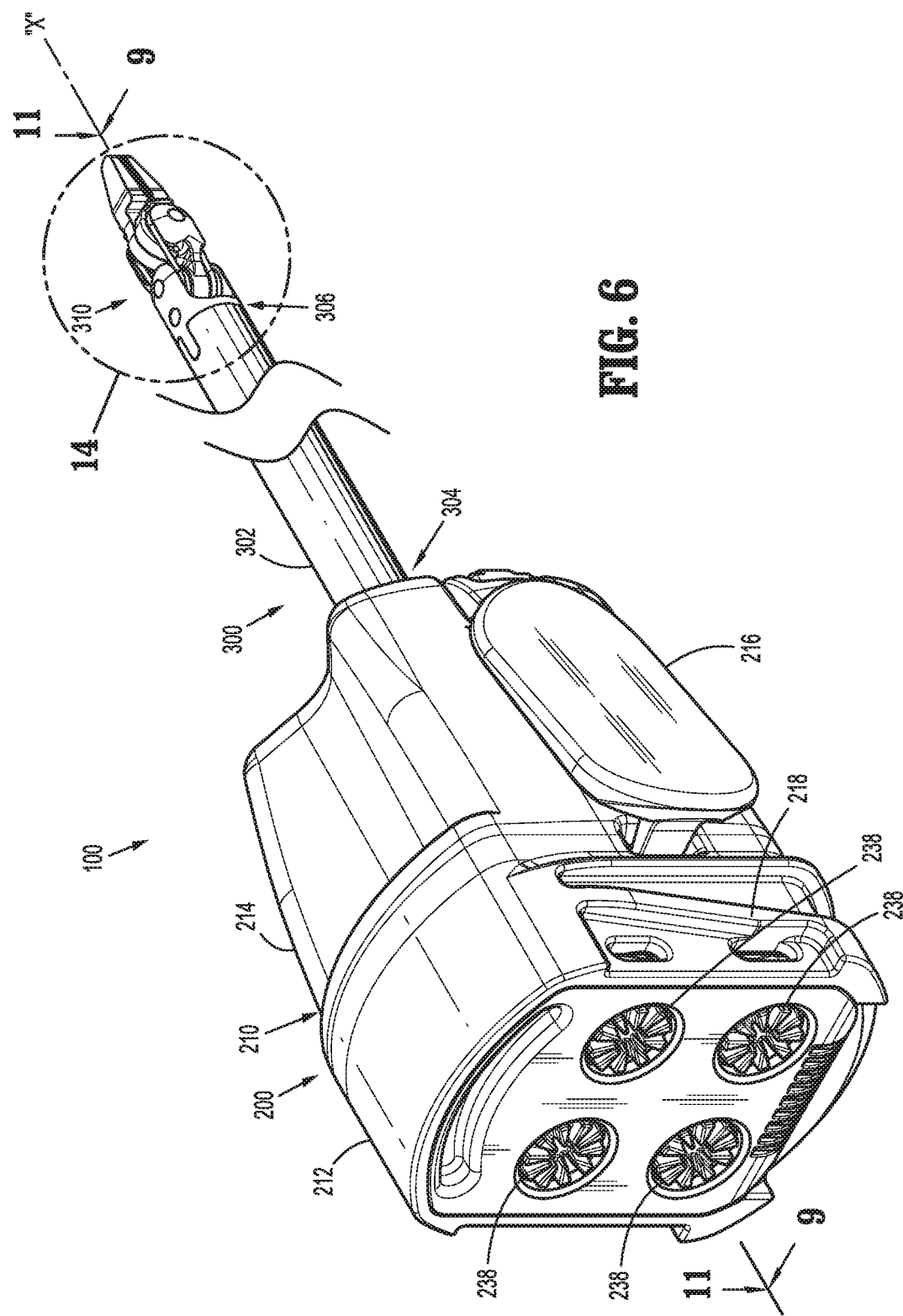
FIG. 6 is an enlarged perspective view of the surgical instrument of FIG. 5.
Figure 7:
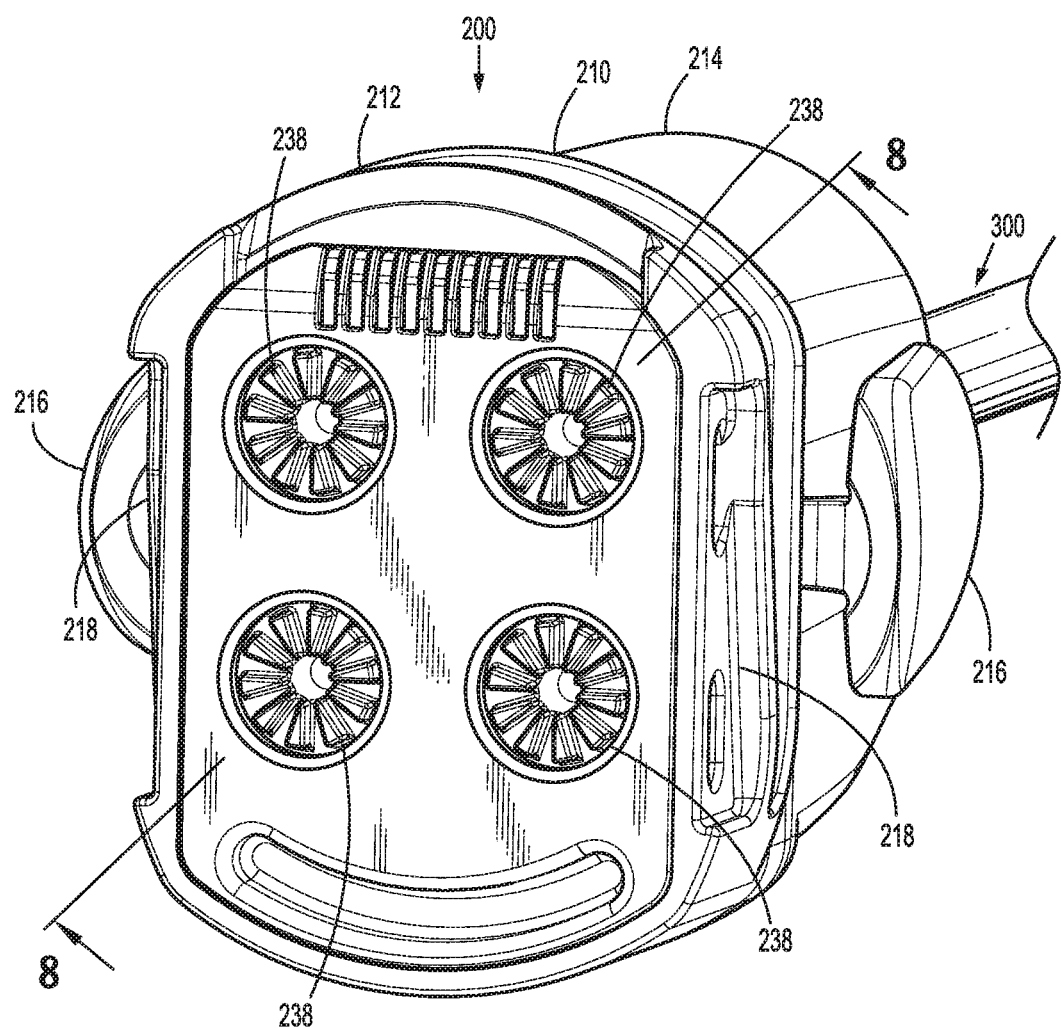
FIG. 7 is a perspective, end view of an instrument drive connector of the surgical instrument of FIGS. 5 and 6.

Referring now to FIGS. 5-7, instrument drive connector 200 of surgical assembly 10 includes a housing assembly 210 which includes a proximal housing 212 and a distal housing 214. Proximal housing 212 and distal housing 214 are releasably coupled to each other, which may facilitate assembly of instrument drive connector 200, and which may facilitate access, repair, and/or replacement of parts housed at least partially therein. Housing assembly 210 may include cantilevered arms 216 configured for use in disconnecting instrument drive connector 200 from distal end 64 of housing 60 of instrument drive unit 50. Proximal housing 212 of housing assembly 210 includes ramped camming surfaces 218 disposed on opposed side surfaces thereof for transverse connection/disconnection with complementary mating surfaces (not shown) of instrument drive unit 50 (FIG. 2).

With reference now to FIGS. 8-12, housing assembly 210 defines a bore 211 which houses a plurality of drive assemblies 220 supported by a drive assembly frame 270. Each drive assembly 220 includes a drive screw 230, a drive nut 240, and a biasing element 250, and is operatively connected to a drive member or rod 260. Drive assembly frame 270 includes a proximal end 272 having a plurality of proximal bearings 274 in which proximal ends 232 of drive screws 230 are retained. Each proximal bearing 274 permits or facilitates rotation of drive screw 230 with respect to housing assembly 210. Additionally, proximal bearings 274 may be configured to function as a proximal stop for drive nut 240. Proximal bearings 274 are disposed radially around a proximal end of an elongated central shaft 276. A plurality of longitudinally extending grooves 278 (FIG. 10) are defined in an outer surface 276a of central shaft 276. Each groove 278 is configured to slidingly engage a proximal end portion 262 of drive members 260 and second rail 248 of drive nut 240.

Figure 12:
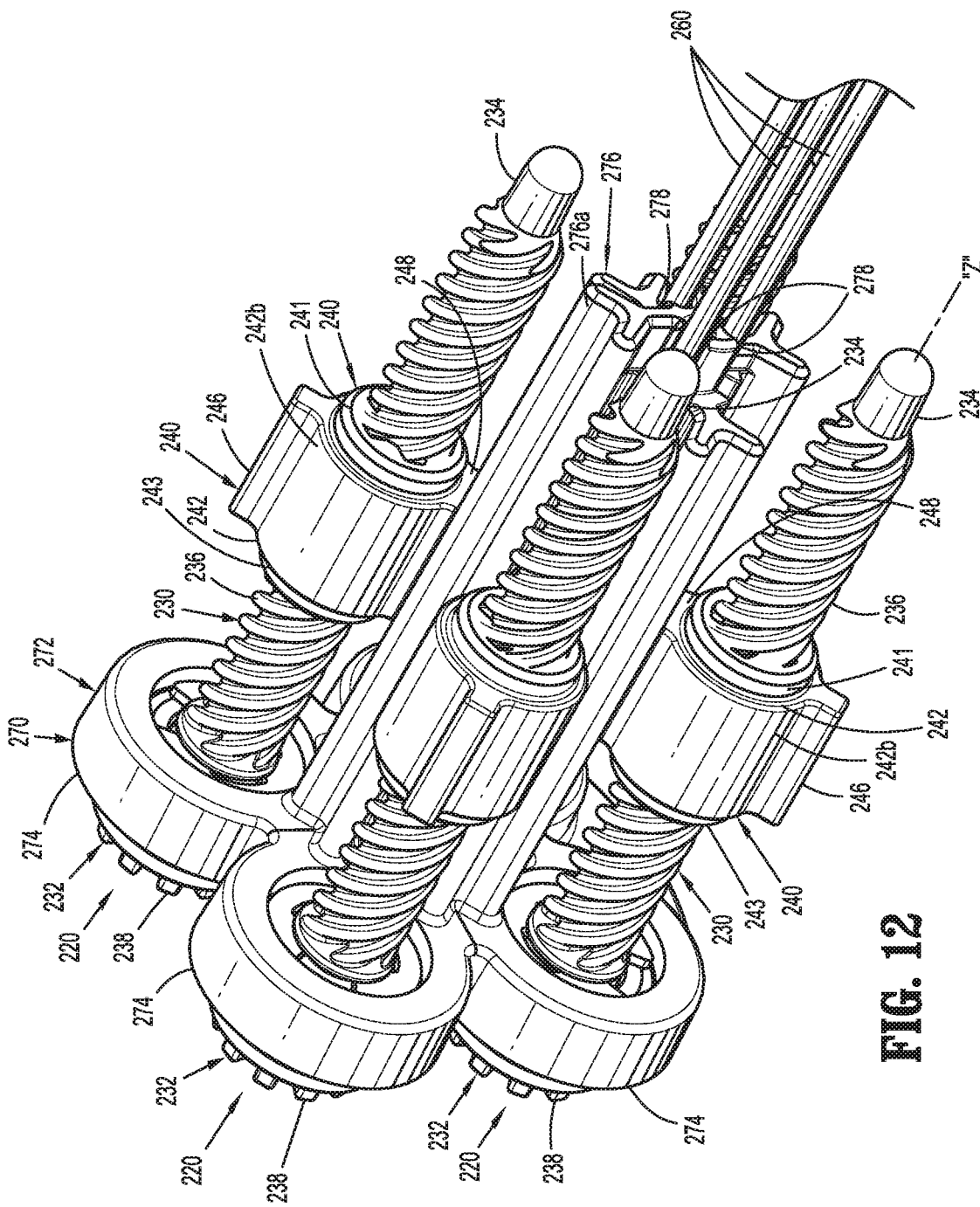
FIG. 12 is a perspective view of a drive assembly disposed within the instrument drive connector of FIGS. 5-11.

As shown in FIG. 12, drive screw 230 includes a proximal end 232, a distal end or tip 234 that is non-threaded, and an elongated threaded body 236 extending between proximal and distal ends 232 and 234, and defines a longitudinal axis "Z" through a radial center thereof. Proximal end 232 of drive screw 230 includes an input drive coupler 238 that is configured to engage with respective output drive couplers 70 of instrument drive unit 50 (FIG. 3) such that movement of output drive couplers 70 cause a corresponding movement of input drive coupler 238. As input drive coupler 238 is monolithically formed with elongated threaded body 236, rotation of input drive coupler 238 results in a corresponding rotation of elongated threaded body 236. It should be understood that input drive coupler 238 and elongated threaded body 236 may be separate components that are keyed to one another. In some embodiments, input drive coupler 238 may be a gear, such as a crown gear, that is configured to mate and/or mesh with a respective crown gear 70 of motor "M1-M4" (FIG. 3), such that rotation of crown gear 70 causes a corresponding rotation of crown gear 238.

Figure 8:
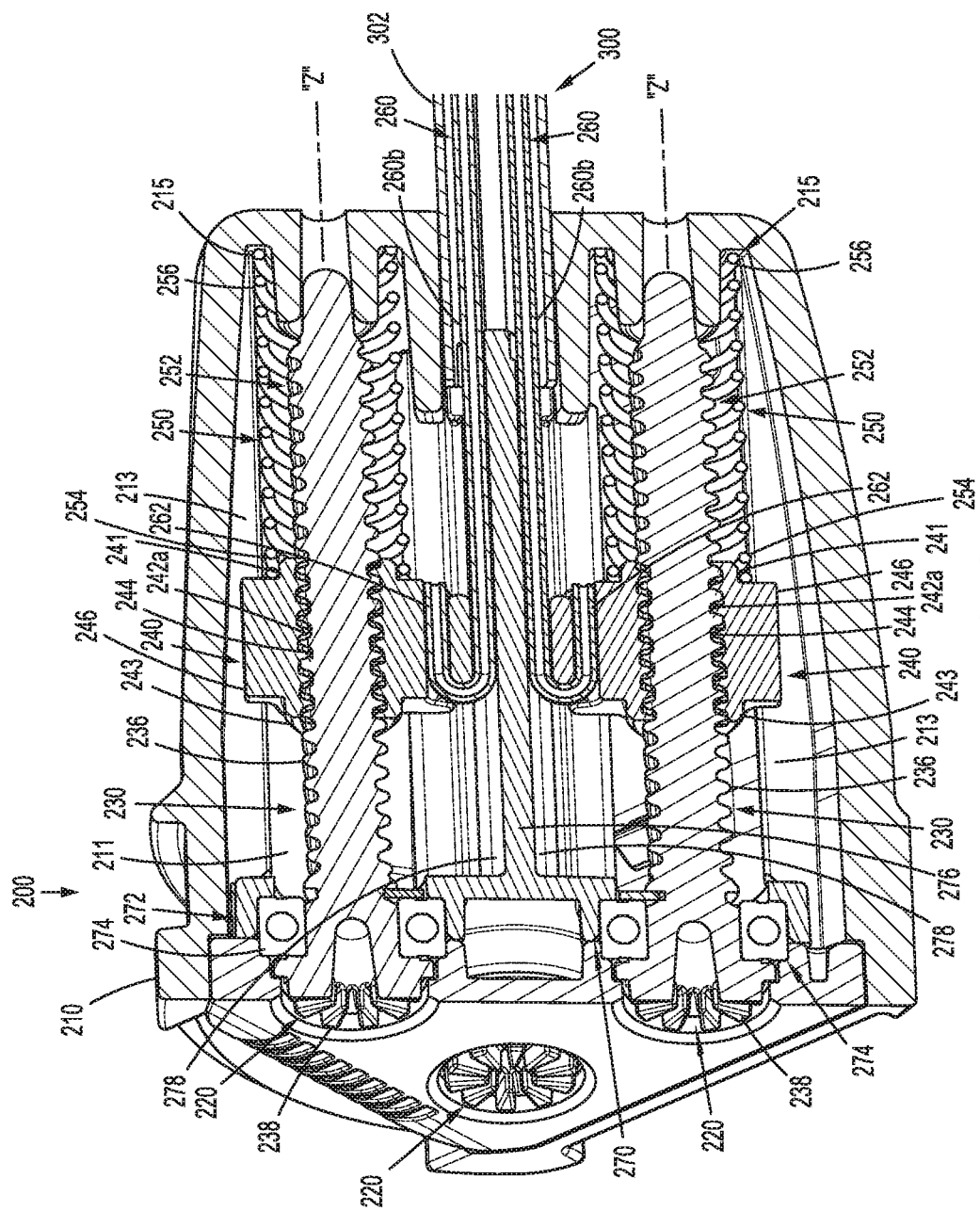
FIG. 8 is a cross-sectional view of the instrument drive connector of the surgical instrument of FIGS. 5-7, taken along line 8-8 of FIG. 7.

As shown in FIGS. 8 and 12, drive nut 240 includes a body 242 having a threaded aperture 244 extending longitudinally through an inner surface 242a thereof which is configured to mechanically engage the elongated threaded body 236 of drive screw 230. Drive nut 240 is configured to be positioned on drive screw 230 in a manner such that rotation of drive screw 230 causes longitudinal movement of drive nut 240. In embodiments, drive nut 240 and drive screw 230 are threadedly engaged with each other. Moreover, rotation of input drive coupler 238 in a first direction (e.g., clockwise) causes drive nut 240 to move in a first longitudinal direction (e.g., proximally) with respect to drive screw 230, and rotation of input drive coupler 238 in a second direction (e.g., counter-clockwise) causes drive nut 230 to move in a second longitudinal direction (e.g., distally) with respect to drive screw 230.

Drive nut 240 includes a first rail 246 extending longitudinally along an outer surface 242b of body 242, and which is configured to be slidably disposed in a longitudinally extending channel 213 formed in bore 211 of housing assembly 210. First rail 246 of drive nut 240 cooperates with channel 213 of bore 211 of housing assembly 210 to inhibit or prevent drive nut 240 from rotating about longitudinal axis "Z" as drive screw 230 is rotated. Drive nut 240 also includes a second rail 248 extending longitudinally along an outer surface 242b of body 242 which is configured to be slidably disposed in longitudinally extending groove 278 formed in drive assembly frame 270. Second rail 248 is configured to mechanically engage a proximal end portion 262 of drive member 260.

Drive nut 240 also includes a retention flange 241 disposed at a distal end of body 242. Retention flange 241 has a smaller outer diameter than body 242 of drive nut 240 and is configured to engage a portion of biasing element 250. Additionally or alternatively, a retention flange 243 may be disposed at a proximal end of body 242 of drive nut 240.

A biasing element 250, e.g., a compression spring, is configured to radially surround a portion of elongated threaded body 236 of drive screw 230. In embodiments, drive screw 230 extends through an aperture 252 defined by and extending longitudinally through biasing element 250. Additionally, as seen in FIG. 8, a proximal portion 254 of biasing element 250 is configured and dimensioned to engage retention flange 241 of drive nut 230 and a distal portion 256 of biasing element 250 is configured and dimensioned for reception at least partially within a retention pocket 215 formed in bore 211 of housing assembly 210. While the illustrated embodiment shows a particular type of biasing element (i.e., a compression spring), other types of biasing elements are contemplated by the present disclosure. Further still, it is contemplated that other retaining structures may be utilized for engagement with a biasing element.

Figure 9:
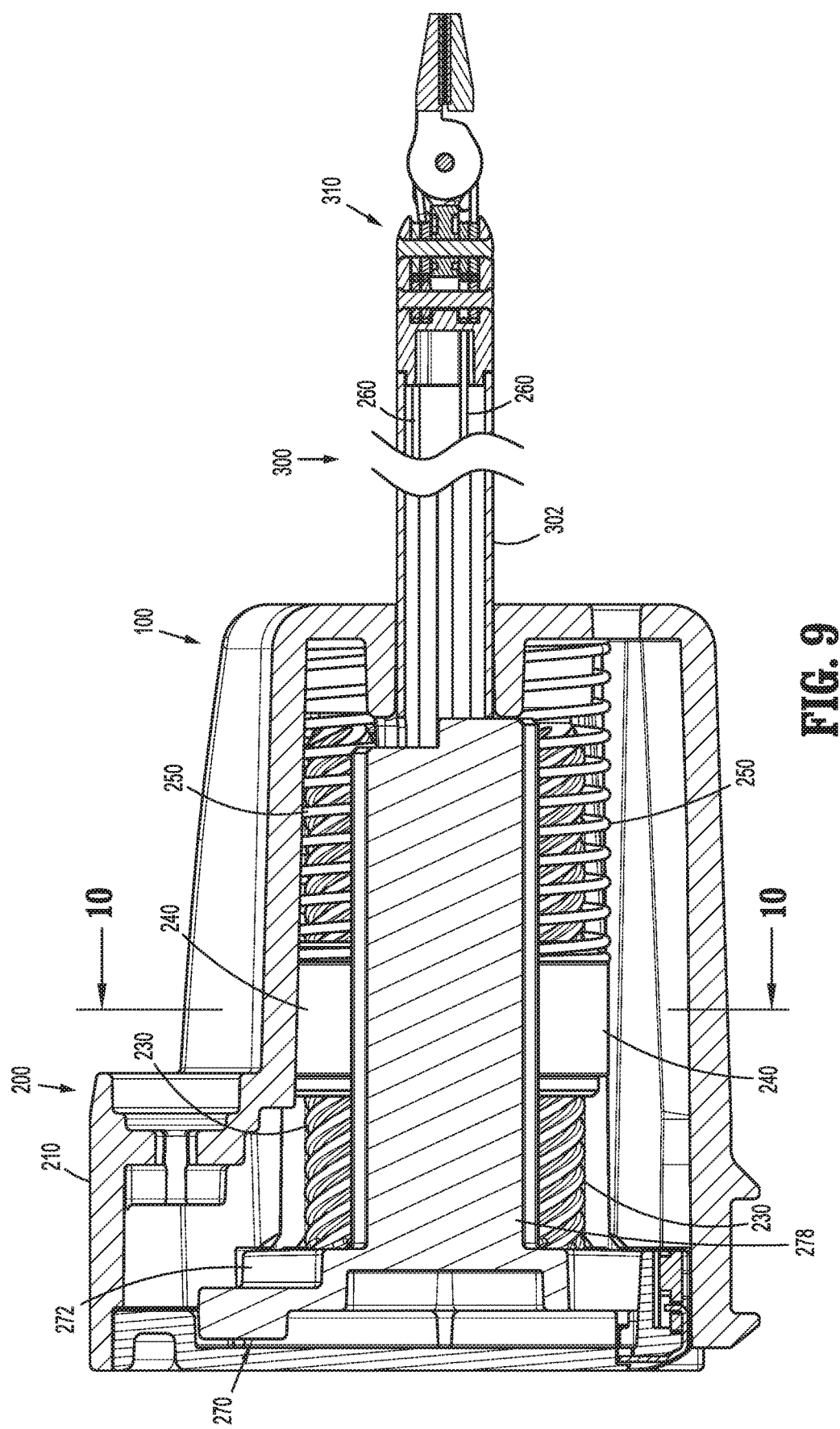
FIG. 9 is a cross-sectional view of the instrument drive connector of the surgical instrument of FIGS. 5-8, taken along line 9-9 of FIG. 6.
Figure 10:
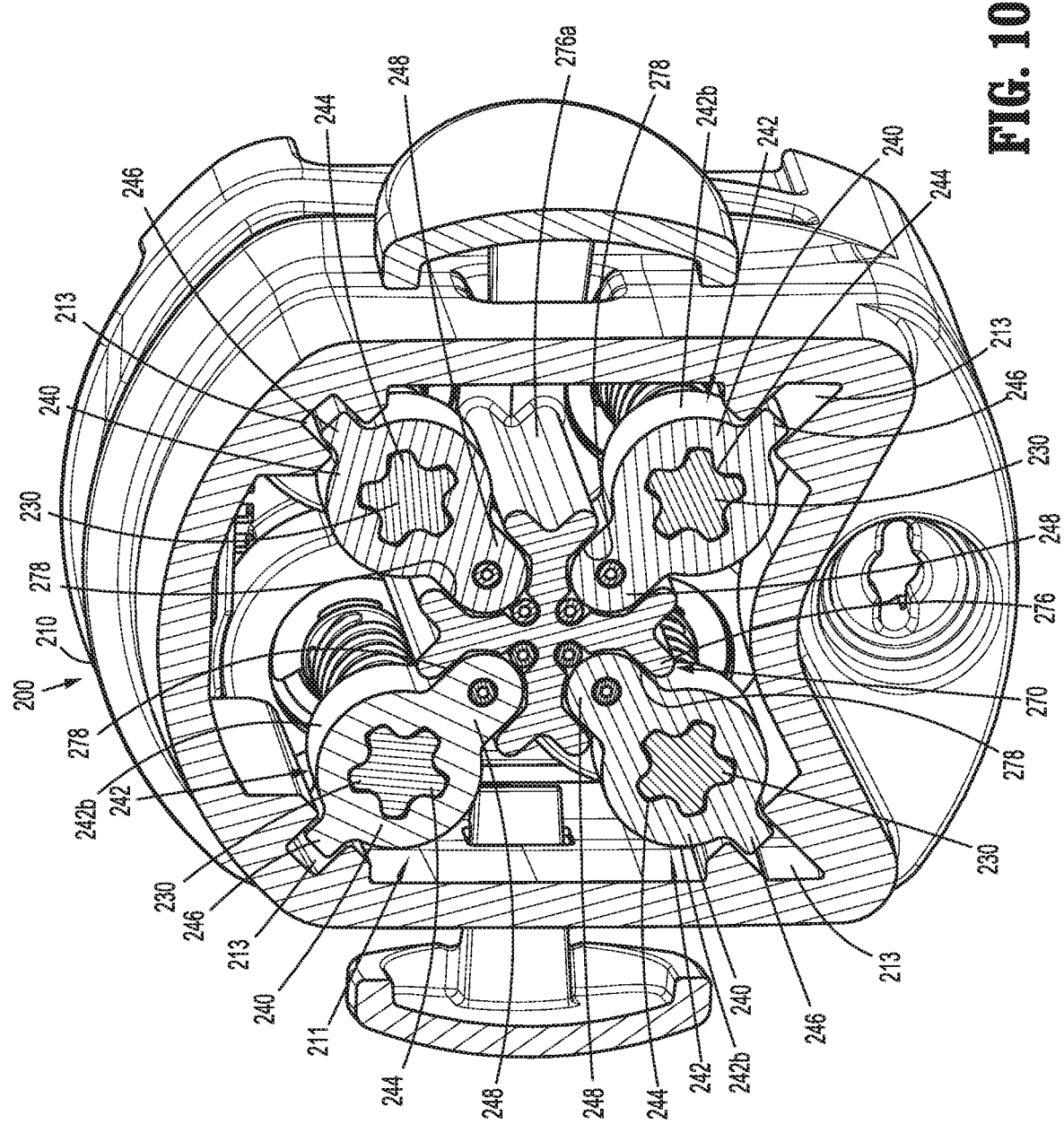
FIG. 10 is a perspective, cross-sectional view of the instrument drive connector of the surgical instrument of FIGS. 5-9, taken along line 10-10 of FIG. 9.
Figure 11:
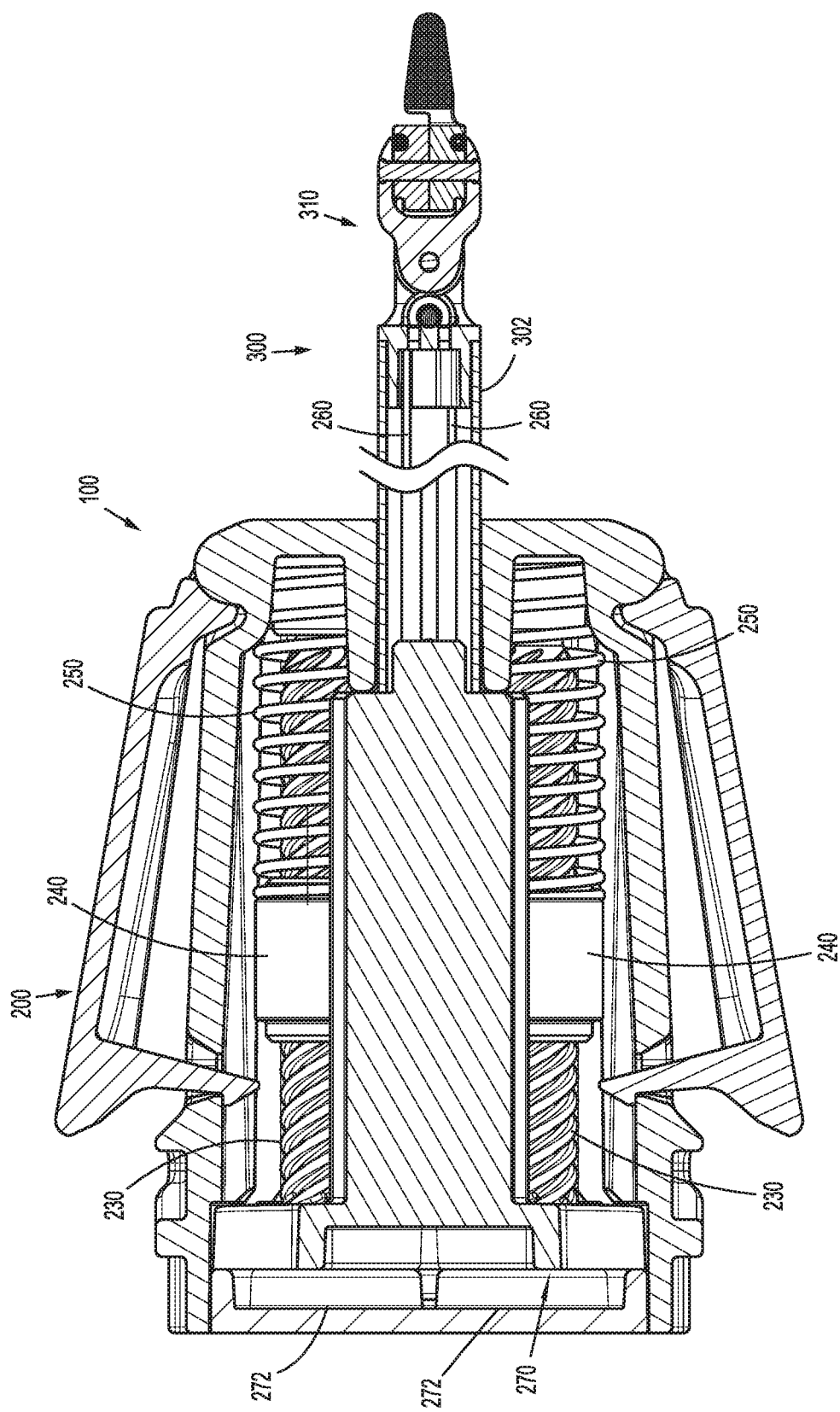
FIG. 11 is a cross-sectional view of the instrument drive connector of the surgical instrument of FIGS. 5-10, taken along line 11-11 of FIG. 6.

Each drive member 260 (e.g., cables, chains, belts, rods, etc. and/or combinations thereof) includes a proximal end portion 262 secured to a respective drive nut 240. Each drive member 260 extends from a respective drive nut 240, through a respective groove 278 of drive assembly frame 270, and out bore 211 of housing assembly 210, and is configured to mechanically engage a portion of end effector 310 (FIG. 9).

Biasing element 250 is pre-tensioned to push a respective drive nut 240 in a proximal direction, thereby applying tension to the respective drive member 260 and preventing drive member 260 from going slack. Drive screw 230, around which biasing element 250 is disposed, is thus back-drivable allowing for manual operation when instrument drive unit 50 is not connected to instrument drive connector 200. Accordingly, when the instrument drive unit 50 is not connected the instrument drive connector 200, a clinician may manually rotate input drive coupler(s) 238 of instrument drive connector 200 to control the surgical instrument 100. For example, when surgical instrument 100 is being retracted from, for example, an access port, and if wrist assembly 320 and/or jaw assembly 330 are in a configuration that would not pass through the orifice formed by the access port, the back-drivability of the drive screws 230 allows wrist assembly 320 and/or jaw assembly 330 to be moved and/or straighten for easy removal of surgical instrument 100 from a patient. As another example, the back-drivability allows for easy manipulation during cleaning of surgical instrument 100 between uses.

Each drive assembly 220 is oriented within housing assembly 210 such that the drive members 260 are centrally located within housing assembly 210, and extends through an elongated shaft 302 of surgical instrument 100 and into engagement with end effector 310, for example. It is envisioned that surgical instrument 100 may include projections or the like to help guide or route drive members 260 between drive assembly 220 and end effector 310.

With reference again to FIGS. 5 and 6, instrument drive connector 200 is configured to transfer rotational movement supplied by instrument control unit 50 (see e.g., FIG. 2) into longitudinal movement of drive members 260 (see e.g., FIG. 8) to effect various functions of end effector 310.

Figure 13:
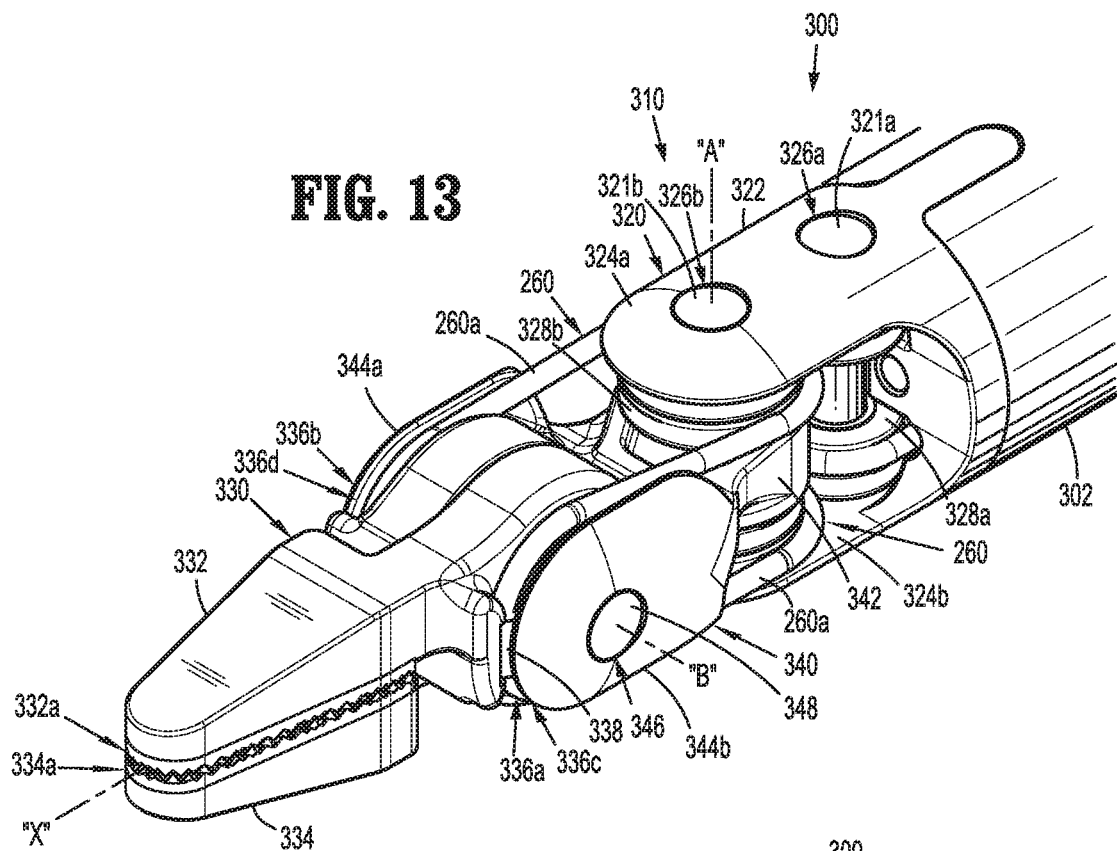
FIG. 13 is enlarged view of the area of detail indicated in FIG. 5.
Figure 14:
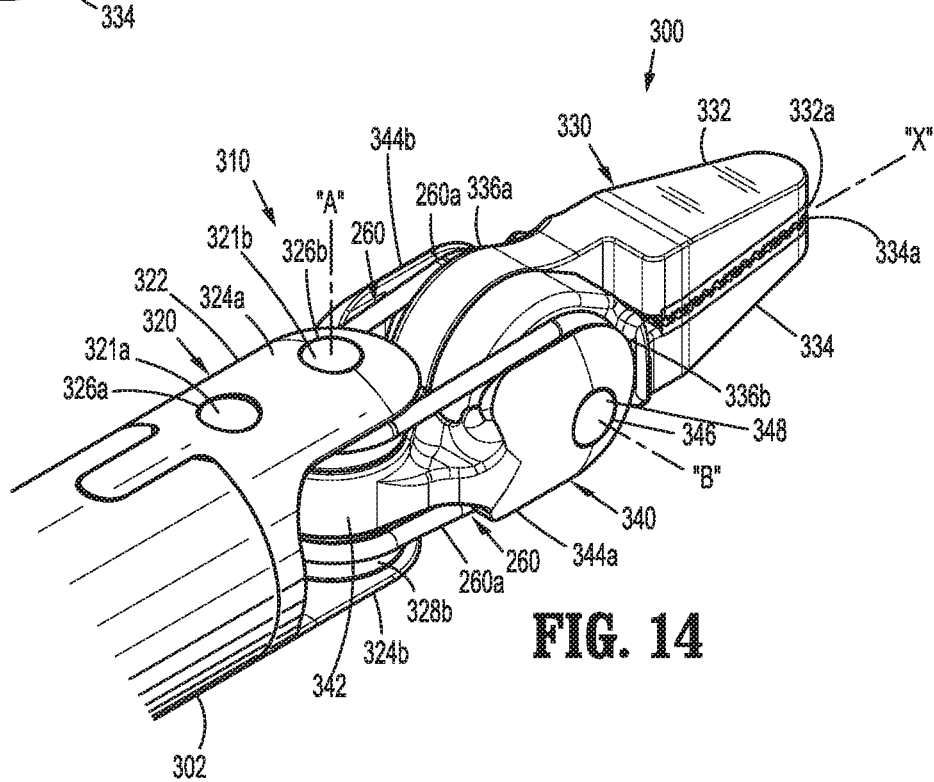
FIG. 14 is enlarged view of the area of detail indicated in FIG. 6.
Figure 15:
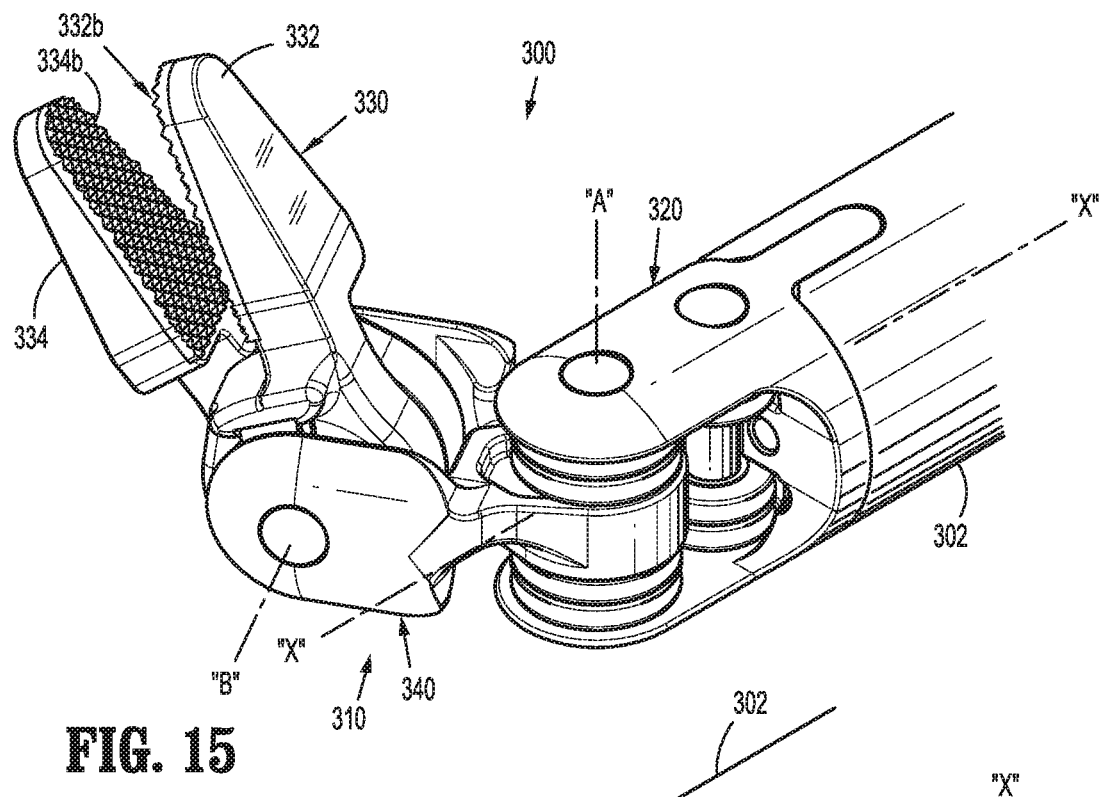
FIG. 15 is a perspective view of an end effector of the surgical instrument of FIGS. 5, 6, 13, and 14 with drive members removed therefrom.

Referring now to FIGS. 13-15, in conjunction with FIGS. 5 and 6, surgical instrument 100 includes an endoscopic portion 300 including an elongated shaft 302 extending along longitudinal axis "X." Elongated shaft 302 includes a proximal portion 304 operably connected to or integrally formed with instrument drive connector 200 and a distal portion 306 having an end effector 310. End effector 310 is a wristed surgical device including a mounting member or wrist assembly 320, a jaw assembly 330, and a clevis 340 connecting the wrist assembly 320 with the jaw assembly 330. Wrist assembly 320 and clevis 340 are connected to jaw assembly 330 which moves (e.g., pivots, articulates, rotates, opens, and/or closes) about/relative to longitudinal axis "X" and/or about/relative to pivot axes, such as axis "A" and "B," upon movement of drive member(s) 260.

Wrist assembly 320 has a mount body 322 that extends distally to a pair of spaced-apart arms including a first arm 324a and a second arm 324b. The pair of spaced-apart arms 324a and 324b defines a first pin channel 326a and a second pin channel 326b that extend transversely through each of first and second arms 324a and 324b. Wrist assembly 320 supports a first set of idler pulleys 328a and a second set of idler pulleys 328b that are aligned with first and second pin channels 326a and 326b, respectively, such that the first set of idler pulleys 328a is located proximal of second set of idler pulleys 328b. First and second sets of idler pulleys 328a and 328b are secured to wrist assembly 320 via first and second pulley pins 321a and 321b, respectively. Second pulley pin 328b and second set of idler pulleys 326b define a pivot axis "A" about which first and second jaw members 332 and 334 pitch relative to longitudinal axis "X."

Jaw assembly 330 includes a first jaw member 332 and a second jaw member 334 that are pivotably coupled together. First jaw member 332 includes a grasping portion 332a that extends distally from a first jaw pulley 336a. Second jaw member 334 includes a grasping portion 334a that extends distally from as second jaw pulley 336b. First and second jaw pulleys 336a and 336b may be integrally formed with grasping portions 332a, 334a, respectively, of first and second jaw members 332 and 334. Grasping portions 332a and 334a include respective tissue-engaging surfaces 332b, 334b configured to engage tissue. First and second jaw pulleys 336a and 336b define respective first and second drive member channels 336c and 336d configured to receive drive members 260.

Clevis 340 includes a base portion 342 having a pair of spaced-apart fingers 344a and 344b that extend distally from base portion 342. The pair of spaced-apart fingers 344a and 344b define a pin passage 346 that extends transversely therethrough. Base portion 342 is pivotally mounted to second set of idler pulleys 326b by pivot pin 321b to enable jaw assembly 330 to pitch/articulate relative to a longitudinal axis "X" of end effector 310. Jaw pulleys 336a and 336b of jaw assembly 300 are coupled together and mounted between the pair of fingers 344a and 344b of clevis 340 by pivot pin 348 to enable jaw assembly 330 to yaw about pivot axis "B" and/or to open/close jaw assembly 330 about pivot axis "B."

As shown in FIGS. 13 and 14, each drive member 260 includes a distal drive member portion 260a (in the form of a cable or the like) that is routed/wrapped around the set of idler pulleys 328a and 238b and jaw pulleys 336a and 336b. Each drive member 260 further includes a proximal drive member portion 260b (in the form of a rod) that is individually secured to a respective drive nut 240 (see e.g., FIG. 8) of drive assembly 220 so that proximal drive member portion 260b moves in response to movement of respective drive nut 240, as described above. A plurality of ferrules 338 (only one being shown) are coupled to the distal drive member portion 260a of drive member 260 to secure distal drive member portion 260a to first jaw member 332 or second jaw member 334 of jaw assembly 330.

In an exemplary method of use, when motor(s) "M1-M4" of instrument drive unit 50 are activated in coordination with one another to rotate (clockwise or counterclockwise) input drive coupler(s) 238 of instrument drive connector 200, rotation of input drive coupler(s) 238 results in a corresponding rotation of respective drive screw(s) 230. Rotation of drive screw(s) 230 causes longitudinal translation (distal or proximal) of respective drive nut(s) 240, with the direction of longitudinal translation of each drive nut 240 being determined by the direction of rotation of its respective output drive coupler 238, and thus drive screw 230. Translation of drive nut(s) 240 results in a corresponding translation of respective drive member(s) 260 which are engaged with drive nut(s) 240.

Figure 16:
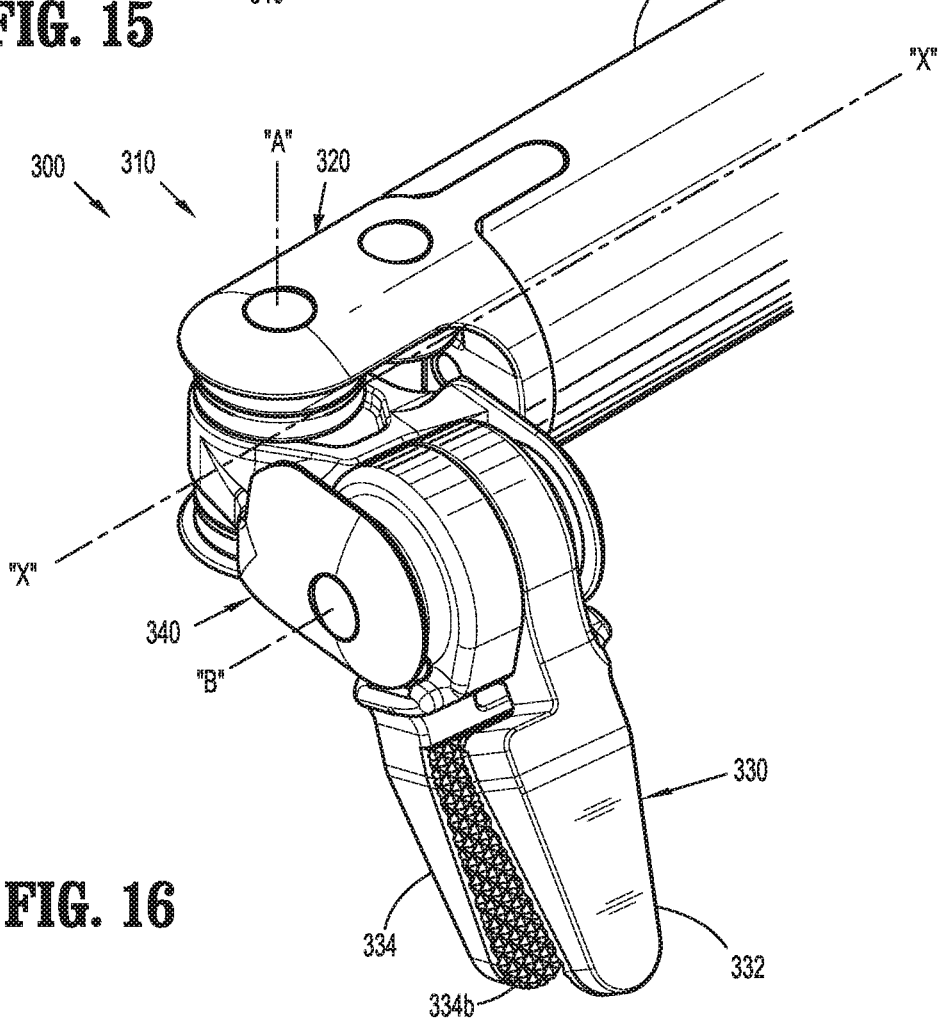
FIG. 16 is a perspective view of the end effector of the surgical instrument of FIGS. 5, 6, and 13-15 with drive members removed therefrom.

Accordingly, one or more of proximal drive member portions 260b of drive members 260 can be moved independently of and/or simultaneously with one or more of the other proximal drive member portions 260b of drive member 260 in the same and/or in opposite directions to effectuate pitching, yawing, grasping/dissecting, opening/closing, and/or any combination of these motions of end effector 310, as shown for example in FIGS. 15 and 16. In some embodiments, drive assemblies 220 utilize differential tension of drive members 260 to effect operation and/or movement of end effector 310 of surgical instrument 100.

While certain embodiments have been described, other embodiments are possible.

Figure 17:
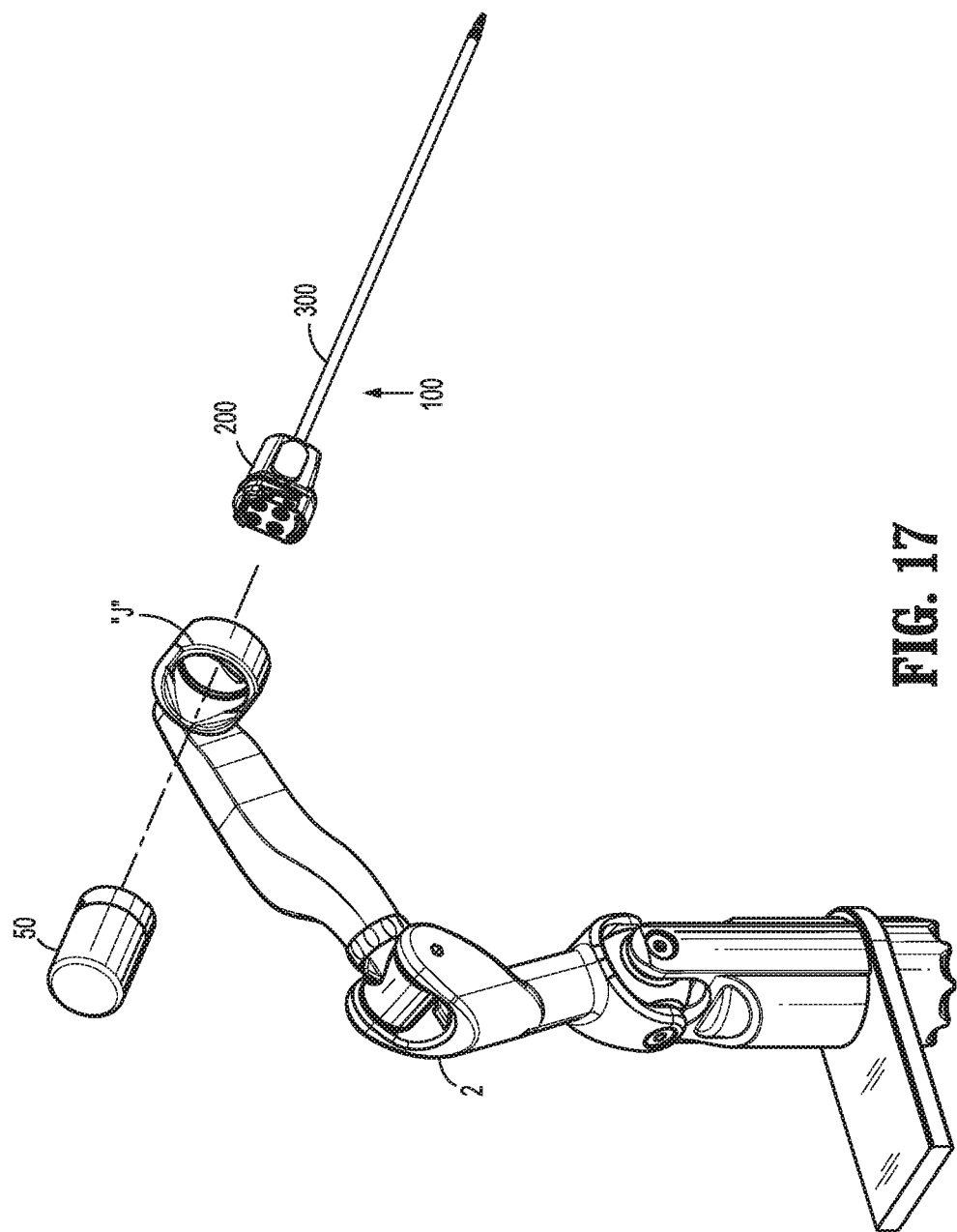
FIG. 17 is a perspective view of a robotic arm of a robotic surgical system including a surgical assembly with parts separated in accordance with the present disclosure.

For example, while instrument drive units have been described as being movably connected to a track of a robotic arm, other configurations are additionally or alternatively possible. For example, as shown in FIG. 17, instrument drive unit 50 may be directly coupled to a joint "J" disposed at a distal end of robotic arm 2. Instrument drive connector 200 of surgical instrument 100 may be connected/disconnected to instrument drive unit 50, as described above.

As another example, while instrument drive connectors have been described as including four drive assemblies, instrument drive connectors may include more (e.g., five or six) or fewer (e.g., two or three) drive assemblies without departing from the scope of the present disclosure.

Additionally, while drive assembly frames have been described as being a component of a drive assembly, the entire structure of a drive assembly frame, or portions thereof, may be integrally formed within the housing assembly of an instrument drive connector.

As still another example, while end effectors have been described as including a jaw assembly, the use of other end effectors are additionally or alternatively possible. Reference may be made to commonly owned International Patent Application No. PCT/US14/61329, filed on Oct. 20, 2014 entitled "Wrist and Jaw Assemblies for Robotic Surgical Systems," the entire content of which is incorporated herein by reference, for a detailed discussion of illustrative examples of the construction and operation of end effectors for use with an instrument drive unit.

As yet another example, while two proximal end portions of a single drive member are shown coupled to separate drive nuts, it is contemplated that two or more proximal end portions of two or more drive members or two proximal end portions of a single drive member may be coupled to a single drive nut. For example, two proximal end portions of a drive member may be coupled in opposite directions to a single drive nut so that as the drive nut is translated in a first direction, one of the proximal end portions winds up while the other proximal end portion lets out.

As another example, each drive assembly may include a drive member in mechanical cooperation with a drive nut and the end effector, such that each drive member includes a single proximal end portion connected to a drive nut and a distal end portion coupled to an end effector to effect a function of the end effector. For example, distal translation of a particular drive member may be configured to approximate jaw members with respect to each other and proximal translation may be configured to move at least one jaw member away from the other jaw member. Further, distal translation of a drive member of a different drive assembly may be configured to articulate jaw members in a first direction, and proximal translation of the same drive member may be configured to articulate jaw members in a second direction.

A number of embodiments have been described. Nevertheless, it will be understood that various modifications may be made to the embodiments disclosed herein. Therefore, the above description should not be construed as limiting, but merely as exemplifications of various embodiments. Those skilled in the art will envision other modifications within the scope and spirit of the disclosure. Accordingly, other embodiments are within the scope of the following claims.

What is claimed is:

1. A surgical instrument for use with and for selective connection to an instrument drive unit, the surgical instrument comprising:
    an end effector defining a longitudinal axis;
    an instrument drive connector including a housing assembly, and a plurality of drive assemblies at least partially disposed within the housing assembly, each drive assembly of the plurality of drive assemblies including:
        a drive screw including an elongated threaded body and being rotatably supported within the housing assembly; and
        a drive nut threadedly engaged with the elongated threaded body of the drive screw such that rotation of the drive screw results in longitudinal movement of the drive nut; and
    a plurality of drive members in mechanical cooperation with the instrument drive connector and the end effector, each drive member of the plurality of drive members including a flexible distal end portion and a rigid proximal end portion secured to a respective drive nut of one of the plurality of drive assemblies such that longitudinal translation of the respective drive nut causes longitudinal translation of the drive member to drive a function of the end effector.

2. The surgical instrument according to claim 1, wherein each drive screw of the plurality of drive assemblies includes a proximal end having an input drive coupler configured to receive rotational forces.

3. The surgical instrument according to claim 1, wherein each drive nut of the plurality of drive assemblies includes a first rail extending longitudinally along an outer surface thereof, the first rail slidingly disposed within a longitudinally extending channel formed within the housing assembly.

4. The surgical instrument according to claim 1, wherein the instrument drive connector includes a drive connector frame disposed within the housing assembly and in mechanical cooperation with the plurality of drive assemblies.

5. The surgical instrument according to claim 4, wherein the drive connector frame includes a proximal end including a plurality of proximal bearings, each bearing of the plurality of proximal bearings dimensioned to retain a proximal end of the drive screw of one of the plurality of drive assemblies.

6. The surgical instrument according to claim 5, wherein the drive connector frame includes an elongated central shaft, and the plurality of proximal bearings are disposed radially around the elongated central shaft.

7. The surgical instrument according to claim 6, wherein the elongated central shaft includes a plurality of longitudinally extending grooves defined in an outer surface thereof, each groove of the plurality of longitudinally extending grooves configured to slidingly receive a portion of a respective one of the plurality of drive members.

8. The surgical instrument according to claim 7, wherein each of the drive nuts of the plurality of drive assemblies includes a second rail extending longitudinally along an outer surface thereof, the second rail slidingly disposed within one of the plurality of longitudinally extending grooves of the elongated central shaft of the drive connector frame.

9. The surgical instrument according to claim 1, wherein the plurality of drive members includes a first drive member and a second drive member, and wherein the end effector includes first and second jaw members and first and second jaw pulleys, the first drive member engaged with the first jaw pulley and the second jaw member engaged with the second jaw pulley such that longitudinal translation of the first and/or second drive members yaws the first and second jaw members about a first pivot axis that is orthogonal to the longitudinal axis of the end effector and/or moves the first and/or second jaw members relative to each other.

10. The surgical instrument according to claim 9, wherein the end effector includes a clevis pivotally mounted to a set of idler pulleys, the first and second jaw pulleys are coupled to the clevis and the first and second drive members are engaged with the set of idler pulleys such that longitudinal translation of the first and/or second drive members pitches the first and second jaw members about a second pivot axis that is orthogonal to both the first pivot axis and the longitudinal axis of the end effector.

11. An instrument drive connector for selectively interconnecting a surgical instrument having an end effector that is configured to perform a function and an instrument drive unit that is configured to actuate the end effector, the instrument drive connector comprising:

a housing assembly defining a bore;
a plurality of drive assemblies at least partially disposed within the bore of the housing assembly, each drive assembly of the plurality of drive assemblies including:
a drive screw including an elongated threaded body and being rotatably supported within the housing assembly; and
a drive nut threadedly engaged with the elongated threaded body of the drive screw such that rotation of the drive screw results in longitudinal movement of the drive nut; and
a plurality of drive members in mechanical cooperation with the instrument drive connector and the end effector, each drive member of the plurality of drive members including a flexible distal end and a rigid proximal end portion secured to a respective drive nut of one of the plurality of drive assemblies such that longitudinal translation of the respective drive nut causes longitudinal translation of the drive member to drive a function of the end effector.

12. The instrument drive connector according to claim 11, wherein each drive screw of the plurality of drive assemblies includes a proximal end having an input drive coupler configured to engage the instrument drive unit and receive rotational forces.

13. The instrument drive connector according to claim 11, wherein each drive nut of the plurality of drive assemblies includes a first rail extending longitudinally along an outer surface thereof, the first rail slidingly disposed within a longitudinally extending channel formed in the bore of the housing assembly.

14. The instrument drive connector according to claim 11, wherein the instrument drive connector includes a drive connector frame disposed within the bore of the housing assembly and in mechanical cooperation with the plurality of drive assemblies.

15. The instrument drive connector according to claim 14, wherein the drive connector frame includes a proximal end including a plurality of proximal bearings, each bearing of the plurality of proximal bearings dimensioned to retain a proximal end of the drive screw of one of the plurality of drive assemblies.

16. The instrument drive connector according to claim 15, wherein the drive connector frame includes an elongated central shaft, and the plurality of proximal bearings are disposed radially around the elongated central shaft.

17. The instrument drive connector according to claim 16, wherein the elongated central shaft includes a plurality of longitudinally extending grooves defined in an outer surface thereof, each groove of the plurality of longitudinally extending grooves configured to slidingly receive a portion of a respective one of the plurality of drive members.

18. The instrument drive connector according to claim 17, wherein each of the drive nuts of the plurality of drive assemblies includes a second rail extending longitudinally along an outer surface thereof, the second rail slidingly disposed within one of the plurality of longitudinally extending grooves of the elongated central shaft of the drive connector frame.

19. A surgical instrument for use with and for selective connection to an instrument drive unit, the surgical instrument comprising:

an end effector defining a longitudinal axis and including first and second jaw member and first and second jaw pulleys;
an instrument drive connector including a housing assembly, and a plurality of drive assemblies at least partially disposed within the housing assembly, each drive assembly of the plurality of drive assemblies including:
   a drive screw including an elongated threaded body and being rotatably supported within the housing assembly; and
   a drive nut threadedly engaged with the elongated threaded body of the drive screw such that rotation of the drive screw results in longitudinal movement of the drive nut; and
a plurality of drive members in mechanical cooperation with the instrument drive connector and the end effector, each drive member of the plurality of drive members including a proximal end portion secured to a respective drive nut of one of the plurality of drive assemblies such that longitudinal translation of the respective drive nut causes longitudinal translation of the drive member to drive a function of the end effector, the plurality of drive members including a first drive member and a second drive member, the first drive member engaged with the first jaw pulley of the end effector and the second jaw member engaged with the second jaw pulley of the end effector such that longitudinal translation of the first and/or second drive members yaws the first and second jaw members about a first pivot axis that is orthogonal to the longitudinal axis of the end effector and/or moves the first and/or second jaw members relative to each other.

20. The surgical instrument according to claim 19, wherein the end effector includes a clevis pivotally mounted to a set of idler pulleys, the first and second jaw pulleys are coupled to the clevis and the first and second drive members are engaged with the set of idler pulleys such that longitudinal translation of the first and/or second drive members pitches the first and second jaw members about a second pivot axis that is orthogonal to both the first pivot axis and the longitudinal axis of the end effector.

* * * * *